United States Patent [19]

Glancy

[11] 4,100,918
[45] Jul. 18, 1978

[54] DYNAMIC ORTHOTIC KNEE EXTENSION ASSIST DEVICE

[75] Inventor: John Glancy, Indianapolis, Ind.

[73] Assignee: Indiana University Foundation, Bloomington, Ind.

[21] Appl. No.: 781,123

[22] Filed: Mar. 25, 1977

[51] Int. Cl.² .......................... A61F 3/00; A61F 5/00
[52] U.S. Cl. ............................. 128/80 F; 128/80 G; 3/1; 3/22
[58] Field of Search ................ 128/80 G, 80 F, 80 R, 128/80 C, 80 H; 3/1, 16, 22, 29

[56] References Cited

U.S. PATENT DOCUMENTS

| 1,072,369 | 9/1913 | Spahn | 128/80 F |
| 2,174,719 | 10/1939 | Dresser | 128/80 F |
| 2,536,454 | 1/1951 | McIntyre | 128/80 G X |
| 2,573,866 | 11/1951 | Murphy | 128/80 F |
| 2,827,897 | 3/1958 | Pawlowski | 128/80 F |

FOREIGN PATENT DOCUMENTS

| 539,210 | 3/1922 | France | 128/80 G |
| 349,864 | 6/1937 | Italy | 128/80 G |

Primary Examiner—Ronald L. Frinks
Attorney, Agent, or Firm—Kirkland & Ellis

[57] ABSTRACT

This application discloses a dynamic knee extension assist device for paraplegic patients and others needing such a device. Cuffs adapted to be secured to a patient's thigh are provided along with mounting means adapted to be secured to a patient's leg below the knee. An elongated elastic member is provided with a means for removably mounting each end thereof to the cuff means at a predetermined tension. Also provided is means for pivotally securing the elastic means intermediate its ends to the mounting means. A lateral knee brace is rigidly disposed between the cuff and the mounting means. The elastic member provides a flexion moment when the patient is seated. As the patient arises, the flexion moment progressively diminishes and then converts to a progressively increasing extension moment as the patient continues to rise.

6 Claims, 5 Drawing Figures

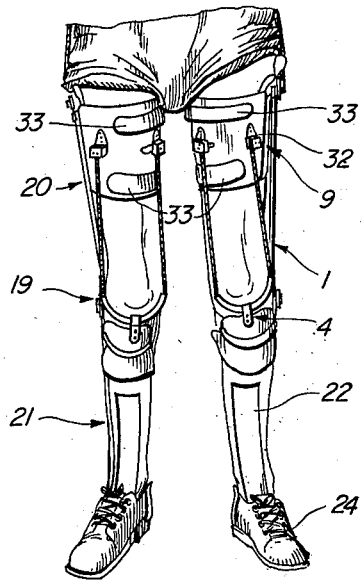
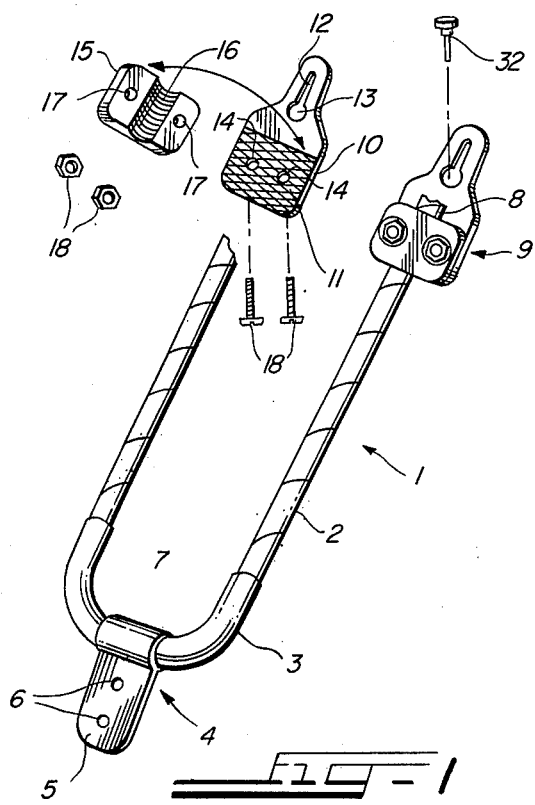
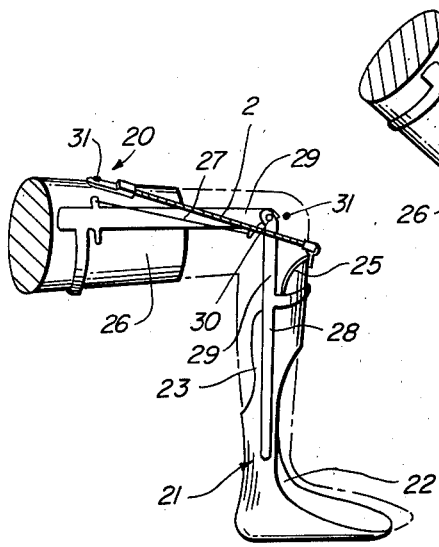
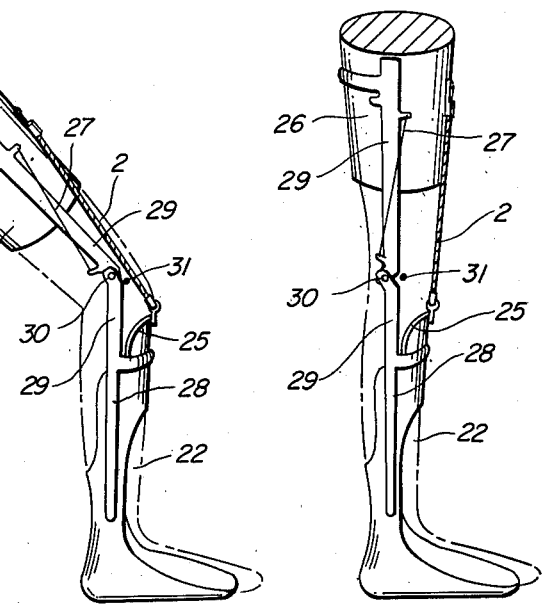

DYNAMIC ORTHOTIC KNEE EXTENSION ASSIST DEVICE

BACKGROUND OF THE INVENTION

1. Field of the Invention

This invention relates to the use of elastic materials as a source of external power in orthotics and more particularly relates to the application of elastic forces in a knee extension assist device.

2. Description of the Prior Art

The current state-of-the-art in orthotics is limited almost exclusively to static control of the musculoskeletal system. As a consequence, freedom of useful motion, in terms of the immediacy of daily living, is constantly subjected to interference. However, removal of static protection often leads to an increase in deformities, followed by an inevitable decrease in daily activities.

In addition, elastic materials can store and deliver significant amounts of dependable energy. The ability to store energy is the most important characteristic of elastic materials for orthotic use. They can be made to produce a continuous force that can be employed in a manner that creates an orthotic system with dynamic forces. The fact that these dynamic forces can be varied in magnitude and made to serve a variety of purposes allows a versatility that far exceeds that of static orthotic systems.

The use of elastic materials as a source of external power can be useful in the development of a practical orthotic system of ambulation for paraplegics and other patients that would enable them to stand and walk with greater ease and confidence than present day static orthotic techniques allow.

The first step in developing a practical means of ambulation for a paraplegic is a system that will enable the patient to get to his feet in a quite conventional manner, starting with the knees flexed in a normal seated position.

Recent improvements in the design of dynamic orthotic systems have permitted the paraplegic patient to rise to a standing position. However, although up, the patient could not extend his knees fully so as to engage the knee locks of the bilateral knee-ankle-foot orthoses. Consequently, the knees buckled at each attempt to bear weight upon the legs. Therefore, further progress was not possible without a mechanism capable of automatically extending the knees and locking them in extension.

Attempts to extend the knee with elastic materials have been numerous with little or no success. The major problem has been that when enough force was applied to provide what could be considered functional extension when standing, the force inadvertently extended the knee when seated.

Accordingly, the primary object of this invention is to provide a practical dynamic orthotic system of ambulation for a paraplegic patient through the application of dynamic forces generated by elastic materials.

A related object is to provide an orthotic system employing dynamic forces to provide the patient with significant assistive force to aid in both rising from and descending to a sitting position.

Another objective is to provide a practical dynamic orthotic system for long-term protection of the musculoskeletal system from deformities without sacrificing the patient's freedom of mobility.

A still further object is to provide a knee extension assist device that may be employed by non-paraplegic patients such as polio victims or others lacking in the muscular structure to adequately extend the knee.

SUMMARY OF THE INVENTION

The foregoing and other objects, advantages and features of the present invention may be achieved with a dynamic knee extension assist device comprising cuff means adapted to be secured to a patient's thigh; mounting means adapted to be secured to the patient's leg below the knee; knee brace means rigidly connecting the cuff means and the mounting means; elongated elastic means capable of exerting a predetermined force; means for adjusting the tension of the elastic means; pivotal means for securing the elastic means intermediate its ends to the pivotal mounting means; and means for removably mounting each end of the elastic means to the cuff means at a predetermined tension. The initial tension of the elastic means is generally preset to provide a force that just exceeds the weight of the patient's leg and that portion of the device lying below the knee axis such that the device provides a controlled knee extension assist.

When the patient is seated, the force generated by the elastic cord is a constant flexion moment. This flexion moment prevents the occurrence of unwanted extension of the lower legs when seated. As the patient arises from the sitting position, the dynamic knee extension assist device initially provides a progressively diminishing flexion moment, thus insuring that the patient's lower legs remain under him until he gets enough of his weight over them to insure that the force of the knee extension assist device will not extend the knee and cause the feet to slide out from under him as he is rising. As the patient continues to rise the flexion moment converts to an extension moment and the magnitude of the extension moment progressively increases as the patient continues to rise. In addition, where the knee brace means is a mechanical offset knee joint, the combination of the mechanical knee axis being behind the anatomical knee axis and the dynamic extension moment generated by the elastic cord results in a remarkably stable knee in the standing position even without utilization of locking devices.

As the patient lowers himself to the sitting position, the dynamic knee extension force generated by the elastic cord offers a substantial resistive force, which acts to slow the patient's descent. The device thus provides both an assistive force aiding the patient in rising from a seated position, and a resistive force slowing his descent.

DESCRIPTION OF THE DRAWINGS

The exact nature and specific details of the invention will be apparent from the following detailed description of the invention when read in conjunction with the annexed drawing in which:

FIG. 1 is an enlarged, partially exploded perspective view of the knee extension assist device of this invention.

FIG. 2 is a front elevational view of a patient wearing the knee extension assist device of this invention.

FIGS. 3, 4, and 5 are side elevational views illustrating the pivotable action of the knee extension assist device of this invention.

DETAILED DESCRIPTION OF THE PREFERRED EMBODIMENTS

In accordance with the present invention, a device is obtained which allows a paraplegic patient to both arise from and descend to a seated position by providing a dynamic force to assist extension of the knee.

Referring to FIG. 1, there is shown a dynamic knee extension assist device 1. The device includes an elastic cord 2 which provides the dynamic force. Any convenient elastic material may be used but it is preferred to employ elastic shock cord about 3/16 inch to ¼ inch in diameter. Other suitable elastic materials may be used, such as rubber members, springs, and the like.

The elastic cord 2 passes through a plastic tube 3 which is allowed to rotate in a mount 4. Mount 4 comprises a plate 5, provided with a pair of mounting holes 6 for a purpose that will hereinafter be described, and a sleeve 7 through which tube 3 is passed. Tube 3 is free to pivot about an axis passing longitudinally through sleeve 7, so as to provide a pivotal mounting parallel to the axis of the knee for the elastic cord passing through tube 3.

Substantially, any suitable material may be employed in fabricating the tube 3, but polypropylene has been found to be especially satisfactory.

Each end 8 of the elastic cord 2 is secured in a retainer 9. Retainer 9 preferably comprises a base plate 10, the lower portion of which has a roughened surface 11. Plate 10 has an upwardly extending tab having a slot 12 with an enlarged opening 13 provided at one end thereof for a purpose that will hereinafter appear. Plate 10 also is provided with a pair of holes 14 which are used to secure a mating cover plate 15 thereto. Cover plate 15 has a roughened groove 16 adapted to receive the elastic cord 2, and a pair of holes 17.

When the cover plate 15 is placed over the elastic cord 2 and against plate 10 the holes 17 align with the holes 14. Nuts and bolts 18 are employed to secure cover plate 15 in position over plate 10 and to securely bind the elastic cord 2. In this manner the initial tension of the cord 2 may be preset as described hereinafter.

Substantially, any suitable means of clamping the elastic cord 2 may be employed, but it has been found that a retainer 9 of the type shown and described is especially satisfactory.

FIG. 2 shows the dynamic knee extension assist device 1 applied to a patient wearing a knee-ankle-foot orthosis comprising a single lateral aluminum knee brace 19 which is mounted both to a quadrilateral thigh cuff 20 and to a solid-ankle orthosis 21.

FIG. 3 shows the solid-ankle orthosis 21 comprising a molded plastic shell with anterior 22 and posterior 23 cutouts for ease of application and removal. Solid-ankle orthosis 21 is designed to be worn with a conventional laced shoe 24. The superior-anterior border 25 of the solid-ankle shell 21 is located at the tibial plateau of the patient.

Substantially, any suitable material may be employed in fabricating the shell, but polypropylene has been found to be uniquely satisfactory.

The quadrilateral thigh cuff 20 comprises a polypropylene sleeve 26 which surrounds the upper thigh of the patient and which is held in position by suitable straps 33. FIGS. 3, 4, and 5 illustrate the knee brace 19 comprising upper 27 and lower 28 metal struts with the proximal ends 29 thereof, connected at a pivotal joint 30. The pivotal joint is offset in the posterior direction from a centerline through the struts when in a parallel-vertical position, as shown in FIG. 5, thereby creating a mechanical offset knee joint 30.

Substantially, any suitable material may be employed in fabricating the struts 27 and 28, but it has been found that aluminum is especially satisfactory.

The distal end of the lower strut 28 is secured anteriorly and laterally to the solid-ankle shell 21 by any suitable means. Distal end of the upper strut 27 is secured posteriorly and laterally to the quadrilateral thigh cuff 20 by any suitable means.

The retainer 9 of each dynamic knee extension assist device is mounted to the anterior position of the corresponding quadrilateral thigh cuff 20. Substantially any suitable means of securing could be employed, but it has been found that the use of a plexidur stud 32 of which the slot 12 in the tab of plate 10 slidably fits is particularly convenient for ease of attachment and removal.

The mount 4 of the dynamic knee extension assist is securely mounted to the proximal end of the solid-ankle orthosis 21 by any suitable means such as rivets passing through holes 6.

FIGS. 3, 4, and 5 demonstrate the manner in which dynamic knee extension device 1 functions so that the line of force generated by the elastic cord 2 changes from a flexion moment (when seated) to an extension moment (as the patient rises).

The initial tension of the elastic cord 2 is preset to provide a force that just exceeds the weight of the patient's lower leg and that portion of the device lying below the knee axis. Since the lower leg is generally about 1/15 of a patient's body weight, the elastic cord is generally preset to provide an effective assistive force of approximately 1/15 of the patient's body weight.

With specific reference to FIG. 3, when the patient is in a seated position, the line of force of the elastic cord 2 is below both the mechanical axis 30 of the lateral knee brace 15 and the anatomical axis of the knee 31 because the mount 4 is fixed to the proximal end of the solid-ankle orthosis 21 below the anatomical knee axis 31. The dynamic force of the elastic cord 2, therefore, creates an effective flexion moment about both axes thereby preventing the occurence of unwanted extension of the knees while seated.

With reference to FIGS. 3 and 4, as the patient rises from the sitting position, the elastic cord 2 moves upward toward the mechanical 30 and anatomical 31 knee axes providing for a gradually diminishing flexion moment during the initial 30° of the patient's ascent. This insures that his lower legs will remain under him until his weight is positioned over them so as to insure that the force of the knee extension assist will not extend the knee prematurely causing the feet to slide out from under the patient as he is rising. When the elastic cord 2 passes through the mechanical 30 and anatomical 31 knee axes, the flexion moment, created by the dynamic force of the elastic cord, changes to an extension moment.

With specific reference to FIGS. 4 and 5, the elastic cord 2 provides an extension moment of increasing magnitude as the patient continues to rise. Because the axis of the offset knee joint 30 is positioned behind the anatomical knee axis 31, the magnitude of the extension moment increases as the patient's thighs move forward by increasing the radius from the mechanical axis to the force generated by the elastic cord 2.

With specific reference to FIG. 5, when the patient has reached the standing position, the combination of the positioning of mechanical knee axis 30 behind the anatomical knee axis 31 and the extension moment generated by the elastic cord 2 results in a remarkably stable pair of knees even without utilizing locking devices.

When the patient lowers himself to the sitting position, the knee extension force generated by the elastic cord 2 offers a substantial resistive force which slows his descent. As the elastic cord 2 passes through the mechanical 30 and anatomical 31 knee axes the extension moment changes to a flexion moment and thereby prevents the patient's knee from extending as he nears the sitting position. The advantage to the patient is both an assistive force aiding in rising and a resistive force slowing descent. Accordingly, the dynamic knee extension assist device of this invention thus fulfills a significant role in overcoming the disadvantages of prior art efforts of employing elastic properties to aid in knee extension. In particular, it provides significant assistive force to aid in both rising from and descending to a sitting position. At the same time, it has solved the problem of the inadvertent extension of the knee while the patient is either in the sitting position or beginning to rise from the sitting position.

In addition, the dynamic knee assist device of this invention allows the patient to extend the knees fully in the standing position and provides a remarkably stable pair of knees even without the utilization of locking devices, especially when musculature is insufficient. The device thus provides a practical dynamic orthotic system for the long-term protection of the musculoskeletal system from deformities without sacrificing the patient's freedom of mobility.

Furthermore, the knee extension assist device of this invention may, in addition to the forgoing applications in the case of paraplegics, be employed with ambulatory patients who may require such assistive forces to regulate the acceleration of the leg about the knee joint in order to insure that, at the end of swing phase, the limb is forward of the body in the proper position to receive the body weight without the knee flexing out of phase with the walking cycle. Thus, the device of this invention may have widespread applications with non-paraplegic patients who nonetheless have need of assistive and resistive forces in one or both legs.

I claim:

1. A dynamic knee extension assist orthotic device comprising:
    cuff means adapted to be secured to a patient's thigh;
    mounting means adapted to be secured to the patient's leg below the knee;
    knee brace means rigidly secured between the mounting means and the cuff means;
    elongated elastic means capable of exerting a predetermined force;
    means for adjusting the tension of the elastic means;
    pivotal means for securing the elastic means intermediate its ends to the mounting means; and
    means for removably mounting each end of the elastic means to the cuff means at a predetermined tension;
    whereby, the elastic means provides a controlled knee.

2. A device, as claimed in claim 1, wherein the mounting means comprises solid-ankle orthosis means.

3. A device as claimed in claim 2, wherein the pivotal means comprises sleeve means through which the elastic means passes intermediate its ends, with the elastic means being free to pivot about an axis parallel to the anatomical knee axis as the knee is extended.

4. A device, as claimed in claim 1, and where the knee brace means comprises a pair of lateral members joined to form a pivotal mechanical knee joint, opposed ends of the members being attached to the cuff means and solid-ankle orthosis means, respectively, the axis of the mechanical knee joint being positioned rearwardly from the anatomical knee axis.

5. A device, as claimed in claim 1, wherein the elastic means comprises elastic shock cord means.

6. A device, as claimed in claim 5, when the tension of the shock cord is preset to provide a force that just exceeds the weight of the patient's lower leg and that portion of the device lying below the axis of the knee.

* * * * *